(12) United States Patent
Swords et al.

(10) Patent No.: US 8,298,292 B2
(45) Date of Patent: *Oct. 30, 2012

(54) CRANIOFACIAL IMPLANT

(75) Inventors: Greg Swords, Atlanta, GA (US); Aaron M. Noble, Newnan, GA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 941 days.

This patent is subject to a terminal disclaimer.

(21) Appl. No.: 11/445,560

(22) Filed: Jun. 2, 2006

(65) Prior Publication Data

US 2006/0224242 A1   Oct. 5, 2006

Related U.S. Application Data

(63) Continuation-in-part of application No. 10/517,843, filed as application No. PCT/US2004/011903 on Apr. 16, 2004, now Pat. No. 7,655,047.

(60) Provisional application No. 60/496,684, filed on Aug. 21, 2003, provisional application No. 60/463,036, filed on Apr. 16, 2003.

(51) Int. Cl.
*A61F 2/02* (2006.01)

(52) U.S. Cl. .................................... 623/23.72

(58) Field of Classification Search .... 623/17.17–17.19, 623/23.5–23.76; 606/151, 213, 215
See application file for complete search history.

(56) References Cited

U.S. PATENT DOCUMENTS

| | | |
|---|---|---|
| 2,671,444 A | 3/1954 | Pease |
| 3,048,537 A | 8/1962 | Pall et al. |
| 3,178,728 A | 4/1965 | Christensen |
| 3,579,643 A | 5/1971 | Morgan |
| 4,089,071 A | 5/1978 | Kalnberz et al. |
| 4,164,794 A | 8/1979 | Spector |
| 4,479,271 A | 10/1984 | Bolesky |
| 4,502,161 A | 3/1985 | Wall |
| 4,531,916 A | 7/1985 | Scantlebury et al. |
| 4,535,485 A | 8/1985 | Ashman et al. |
| 4,542,539 A | 9/1985 | Rowe, Jr. et al. |
| 4,550,448 A | 11/1985 | Kenna |
| 4,636,215 A | 1/1987 | Schwartz |
| 4,693,721 A | 9/1987 | Ducheyne |
| 4,756,862 A | 7/1988 | Spector |
| 4,778,472 A | 10/1988 | Homsy et al. |

(Continued)

FOREIGN PATENT DOCUMENTS

CN   1225373 A   8/1999

(Continued)

OTHER PUBLICATIONS

Supplementary Partial European Search Report from EP Appl. No. EP 04759969.1 issued May 2, 2008.

(Continued)

*Primary Examiner* — David Isabella
*Assistant Examiner* — Ann Schillinger
(74) *Attorney, Agent, or Firm* — Lerner, David, Littenberg, Krumholz & Mentlik, LLP

(57) ABSTRACT

A composite surgical implant that is made of a planar sheet of a thermoplastic resin that includes a top surface, a bottom surface, and a surgical grade metal mesh or metal plates contained therein. The implant may be bent by hand, wherein upon the displacement of the implant, the implant will generally maintain the shape to which it has been displaced.

25 Claims, 12 Drawing Sheets

U.S. PATENT DOCUMENTS

| | | |
|---|---|---|
| 4,790,849 A | 12/1988 | Terino |
| 4,863,474 A | 9/1989 | Brown et al. |
| 4,917,701 A | 4/1990 | Morgan |
| 4,936,852 A | 6/1990 | Kent et al. |
| 4,969,901 A | 11/1990 | Binder |
| 4,976,737 A | 12/1990 | Leake |
| 4,976,738 A | 12/1990 | Frey et al. |
| 4,978,355 A | 12/1990 | Frey |
| 5,030,233 A | 7/1991 | Ducheyne |
| 5,139,497 A | 8/1992 | Tilghman et al. |
| 5,201,737 A | 4/1993 | Leibinger et al. |
| 5,218,975 A | 6/1993 | Prostkoff |
| 5,250,048 A | 10/1993 | Gundolf |
| 5,282,861 A | 2/1994 | Kaplan |
| 5,290,315 A | 3/1994 | DeCarlo |
| 5,346,492 A | 9/1994 | Morgan |
| 5,372,598 A | 12/1994 | Luhr |
| 5,380,328 A * | 1/1995 | Morgan ................. 606/70 |
| 5,383,931 A * | 1/1995 | Hehli et al. ............ 623/17.18 |
| 5,397,361 A | 3/1995 | Clark |
| 5,421,831 A | 6/1995 | Giampapa |
| 5,433,996 A | 7/1995 | Kranzler |
| 5,443,512 A | 8/1995 | Pan |
| 5,443,519 A | 8/1995 | Averill |
| 5,445,650 A | 8/1995 | Nealis |
| 5,456,723 A | 10/1995 | Steinemann |
| 5,468,242 A | 11/1995 | Reisberg |
| 5,489,305 A | 2/1996 | Morgan |
| 5,496,371 A | 3/1996 | Eppley et al. |
| 5,496,372 A | 3/1996 | Hamamoto et al. |
| 5,545,226 A | 8/1996 | Wingo |
| 5,554,194 A | 9/1996 | Sanders |
| 5,578,086 A | 11/1996 | Prescott |
| 5,669,909 A | 9/1997 | Zdeblick |
| 5,690,631 A | 11/1997 | Duncan et al. |
| 5,728,157 A | 3/1998 | Prescott |
| 5,743,913 A * | 4/1998 | Wellisz ................. 606/285 |
| 5,755,809 A | 5/1998 | Cohen |
| 5,766,176 A | 6/1998 | Duncan |
| 5,769,637 A | 6/1998 | Morgan |
| 5,814,048 A | 9/1998 | Morgan |
| 5,824,088 A | 10/1998 | Kirsch |
| 5,863,297 A | 1/1999 | Walter et al. |
| 5,876,447 A | 3/1999 | Arnett |
| 5,980,540 A | 11/1999 | Bruce |
| 5,989,427 A | 11/1999 | Ellard et al. |
| 5,989,472 A | 11/1999 | Ashby et al. |
| 6,008,430 A | 12/1999 | White |
| 6,010,336 A | 1/2000 | Shimotoso et al. |
| 6,031,148 A | 2/2000 | Hayes et al. |
| 6,065,197 A | 5/2000 | Iseki et al. |
| 6,071,291 A | 6/2000 | Forst et al. |
| 6,087,553 A | 7/2000 | Cohen |
| 6,093,188 A | 7/2000 | Murray |
| 6,120,539 A | 9/2000 | Eldridge et al. |
| 6,129,728 A | 10/2000 | Schumacher et al. |
| 6,143,036 A | 11/2000 | Comfort |
| 6,187,041 B1 | 2/2001 | Garonzik |
| 6,221,075 B1 | 4/2001 | Törmälä et al. |
| 6,238,214 B1 | 5/2001 | Robinson |
| 6,267,772 B1 | 7/2001 | Mulhauser et al. |
| 6,270,530 B1 | 8/2001 | Eldridge et al. |
| 6,315,798 B1 | 11/2001 | Ashby et al. |
| 6,325,803 B1 | 12/2001 | Schumacher et al. |
| 6,350,284 B1 | 2/2002 | Tormala et al. |
| 6,391,059 B1 | 5/2002 | Lemperle et al. |
| 6,394,807 B2 | 5/2002 | Robinson |
| 6,475,094 B1 | 11/2002 | Bruns et al. |
| 6,530,953 B2 | 3/2003 | Garonzik |
| 6,620,332 B2 | 9/2003 | Amrich |
| 6,645,250 B2 * | 11/2003 | Schulter ............. 623/17.17 |
| 6,652,585 B2 | 11/2003 | Lange |
| 6,692,497 B1 | 2/2004 | Tormala et al. |
| 6,692,498 B1 | 2/2004 | Niiranen et al. |
| 6,827,743 B2 | 12/2004 | Eisermann et al. |
| 6,852,128 B2 | 2/2005 | Lange |
| 6,852,330 B2 | 2/2005 | Bowman et al. |
| 7,041,138 B2 | 5/2006 | Lange |
| 7,050,877 B2 | 5/2006 | Iseki et al. |
| 7,066,962 B2 | 6/2006 | Swords |
| 7,113,841 B2 | 9/2006 | Abe et al. |
| 7,208,222 B2 | 4/2007 | Rolfe et al. |
| 7,326,249 B2 | 2/2008 | Lange |
| 7,341,601 B2 | 3/2008 | Eisermann et al. |
| 7,614,258 B2 | 11/2009 | Cherok et al. |
| 7,655,047 B2 | 2/2010 | Swords |
| 7,662,155 B2 | 2/2010 | Metzger et al. |
| 2001/0012607 A1 | 8/2001 | Robinson |
| 2002/0022883 A1 | 2/2002 | Burg |
| 2002/0050463 A1 | 5/2002 | McDowell |
| 2002/0120348 A1* | 8/2002 | Melican et al. ............ 623/23.72 |
| 2002/0123750 A1* | 9/2002 | Eisermann et al. ............ 606/69 |
| 2003/0208205 A1 | 11/2003 | Gambale |
| 2003/0220696 A1 | 11/2003 | Levine et al. |
| 2004/0019389 A1 | 1/2004 | Swords |
| 2004/0054372 A1 | 3/2004 | Corden et al. |
| 2004/0059356 A1 | 3/2004 | Gingras |
| 2004/0059422 A1 | 3/2004 | Koschatzky et al. |
| 2004/0267349 A1 | 12/2004 | Richter |
| 2005/0043733 A1 | 2/2005 | Eisermann et al. |
| 2005/0146070 A1 | 7/2005 | Muratoglu et al. |
| 2005/0192675 A1 | 9/2005 | Robinson |
| 2005/0208095 A1 | 9/2005 | Hunter et al. |
| 2005/0288790 A1* | 12/2005 | Swords ................. 623/17.19 |
| 2006/0116682 A1 | 6/2006 | Longo |
| 2006/0217813 A1 | 9/2006 | Posnick et al. |
| 2006/0224242 A1 | 10/2006 | Swords et al. |
| 2007/0156146 A1 | 7/2007 | Metzger et al. |
| 2009/0138067 A1* | 5/2009 | Pinchuk et al. ............. 623/1.13 |
| 2009/0216338 A1 | 8/2009 | Gingras et al. |
| 2010/0023130 A1 | 1/2010 | Henry et al. |
| 2010/0076555 A1 | 3/2010 | Marten et al. |

FOREIGN PATENT DOCUMENTS

| | | |
|---|---|---|
| CN | 1225373 | 11/1999 |
| DE | 2404214 | 1/1974 |
| EP | 0 092 260 A | 10/1983 |
| EP | 0 092 260 A1 | 10/1983 |
| EP | 0178650 | 4/1986 |
| EP | 0423420 | 4/1991 |
| EP | 0433852 | 6/1991 |
| EP | 0544384 | 6/1993 |
| EP | 0566255 | 10/1993 |
| EP | 0654250 | 5/1995 |
| EP | 0910993 | 4/1999 |
| GB | 2059267 | 4/1981 |
| JP | 2-237559 | 9/1990 |
| JP | 9-173364 | 7/1997 |
| JP | 11-155879 | 6/1999 |
| WO | 97/41791 A1 | 11/1997 |
| WO | WO 97/41791 A | 11/1997 |
| WO | 99/37240 A2 | 7/1999 |
| WO | WO 99/37240 A | 7/1999 |
| WO | WO02/92882 | 4/2002 |
| WO | 02069817 A1 | 9/2002 |
| WO | WO03/084410 | 4/2003 |
| WO | 03086495 A1 | 10/2003 |
| WO | WO 2004/093743 A1 | 11/2004 |
| WO | 2007142743 A2 | 12/2007 |
| WO | WO-2007142743 A3 | 5/2008 |

OTHER PUBLICATIONS

Marbacher, S. et al., Primary Reconstruction of Open Depressed Skull Fractures With Titanium Mesh; The Journal of Craniofacial Surgery, vol. 19, No. 2, Mar. 2008, pp. 490-495.

U.S. Appl. No. 10/517,843 Office Action dated Jul. 3, 2007.

U.S. Appl. No. 10/517,843 Response to Jul. 3, 2007 OA dated Sep. 4, 2007.

U.S. Appl. No. 10/517,843 Office Action dated Dec. 14, 2007.

U.S. Appl. No. 10/517,843 Response to Dec. 14, 2007 OA dated Mar. 14, 2008.

U.S. Appl. No. 10/517,843 Final Office Action dated Jun. 25, 2008.

Janecka, I. P. "New Reconstructive Technologies in Skull Base Surgery", *Archieves of Otolaryngology Head and Neck Surgery* 2000, vol. 126, 396-401.

First Examination Report for EP04759969.1 issued by the European Patent Office on Sep. 29, 2008.
U.S. Appl. No. 10/517,843 Non-Final Office Action dated Mar. 17, 2009.
2006 ASOPRS Fall Scientific Symposium—Holck.
Choi et al., Ophthalmic Plastic and Reconstructive Surgery, vol. 15, No. 1, pp. 56-66, 1999.
International Search Report for PCT/US07/009471 dated Aug. 8, 2008.
Murakami, N. Saito N., Horiuchi H., et al. (2002): Repair of segmental defects in rabbit humeri with titanium fiber mesh cylinders containing recombinant human bone morphogenetic protein-2 (rhBMP-2) and a synthetic polymer, J Biomed Mat Res,62(2):169-174, Nov. 2002.
Nguyen, Clinics in Plastic Surgery, vol. 19, No. 1, pp. 87-98, Jan. 1992.
Office Action dated Nov. 12, 2009 issued in related U.S. Appl. No. 11/445,560.
Oka M., Ushio K., Kumar P., et al. (2000): Artifical Articular Cartilage, Proc Inst Mech Eng [H], 214(1):59-68,2000.
Park, Hun K., Biomechanical properties of high-density polyethylene for pterional prosthesis, http://findarticles.com, Neurological Research, Oct. 2002.
Porex Surgical Products Group, website printout, www.porexsurgical.com, printed May 13, 2010.
Rubin, Ophthalmology, vol. 101, No. 10, pp. 1697-1708, 1994.
U.S. Appl. No. 11/445,560 Final Office Action dated Nov. 12, 2009.
U.S. Appl. No. 11/445,560 Non-Final Office Action dated Oct. 29, 2008.
U.S. Appl. No. 11/445,560 Office Action dated May 9, 2008.
U.S. Appl. No. 11/445,560 Response to May 9, 2008 OA dated Jun. 2, 2008.
U.S. Appl. No. 11/445,560 Response to Office Action dated Dec. 23, 2008.
U.S. Appl. No. 11/445,560 Second Non-Final Office Action dated Mar. 17, 2009.
Office Action from Russian Application No. 2008152069/15(0684840 dated Dec. 6, 2010.
Civil Docket for Case #: 3:10-cv-00023-JTC Claim Construction Brief filed by Porex Corporation, Porex Surgical, Inc . . . (Attachments: # Exhibit 1, # Exhibit 2, # Exhibit 3, # Exhibit 4, # Exhibit 5).
Civil Docket for Case #: 3:10-cv-00023-JTC First Amended Complaint against Synthes USA Sales, LLC, Synthes North America, Inc., Synthes, Inc., filed by Porex Surgical, Inc., Porex Corporation. (Attachments: Exhibit A).
Civil Docket for Case #: 3:10-cv-00023-JTC Answer to Amended Complaint ( Discovery ends on Jan. 3, 2011.), Counterclaim against all plaintiffs with Jury Demand by Synthes USA Sales, LLC, Synthes North America, Inc., Synthes, Inc.
Civil Docket for Case #: 3:10-cv-00023-JTC Complaint with Jury Demand filed by Porex Surgical, Inc., Porex Corporation and summon(s) issued. (Filing fee $ 350 receipt No. 300000475.) (Attachments: # Exhibit A, # Summons, # Civil Cover Sheet, # AO 120).
Civil Docket for Case #: 3:10-cv-00023-JTC First Claim Construction Brief filed by Synthes North America, Inc., Synthes North America, Inc., Synthes USA Sales, LLC, Synthes USA Sales, LLC.. (Attachments: # Appendix, # Exhibit 1, # Exhibit 2, # Exhibit 3, # Exhibit 4, # Exhibit 5, # Exhibit 6, # Exhibit 7.
Civil Docket for Case #: 3:10-cv-00023-JTC Joint Claim Construction Statement filed by Synthes USA Sales, LLC, Synthes, Inc., Porex Surgical, Inc., Porex Corporation.
Civil Docket for Case #: 3:10-cv-00023-JTC Motion for Leave to File a Sur-Reply in Opposition to Plaintiff's Motion for Preliminary Injunction with Brief in Support by Synthes USA Sales, LLC, Synthes North America, Inc., Synthes, Inc., Synthes USA Sales, LLC, Synthes North America, Inc., Synthes, Inc.. (Attachments: # Exhibit A, # Exhibit B, # Exhibit 21, # Exhibit 22, # Exhibit 23).
Civil Docket for Case #: 3:10-cv-00023-JTC Motion for Preliminary Injunction with Brief in Support by Porex Surgical, Inc., Porex Corporation. (Attachments: # Brief, # Exhibit A, # Exhibit B, # Exhibit C, # Exhibit D, # Exhibit E, # Text of Proposed Order.

Civil Docket for Case #: 3:10-cv-00023-JTC Plaintiffs' Answer to Counterclaim of Defendants by Porex Surgical, Inc., Porex Corporation.
Civil Docket for Case #: 3:10-cv-00023-JTC Reply Brief re Motion for Preliminary Injunction filed by Porex Surgical, Inc., Porex Corporation. (Attachments: # Exhibit A, # Exhibit B).
Civil Docket for Case #: 3:10-cv-00023-JTC Response in Opposition re Motion for Preliminary Injunction filed by Synthes USA Sales, LLC, Synthes North America, Inc., Synthes, Inc.. (Attachments: # Index to Appendix vol. 2 with Certificate of Service, # Exhibits 3 -7, # Exhibits 8-12, # Exhibits 13-17, # Exhibits 18-20) Appendix Sealed Document, # Exhibit 1 Sealed Document, # Exhibit 2 Sealed Document.
Civil Docket for Case #: 3:10-cv-00023-JTC Response in Opposition re Motion for Preliminary Injunction filed by Synthes USA Sales, LLC, Synthes North America, Inc., Synthes, Inc.. (Attachments: # Index to Appendix vol. 2 with Certificate of Service, # Exhibits 3-7, # Exhibits 8-12, # Exhibits 13-17, # Exhibits 18-20)—Exhibit 1 Sealed Document, # Exhibit 2 Sealed Document.
Civil Docket for Case #: 3:10-cv-00023-JTC (U.S. District Court, Northern District of GU.S. District Court, Northern District of Georgia (Newnan)).
W.L. Gore & Associates, Gore-Tex Regenerative Membrane, Instructional broshure, Feb. 2003.
Helfen, et al., 'Zementfreie Pfanne und zementierter Schaft-Konzept einger ..Hybrid-Lösung sowie Ergebnisse einer drei-bis sechsjährigen klinischen Erfahrung,' Z. Ortho., 131:578-584 (1993).
MEDPOR Biomaterials brochure, 05 pages, Porex Surgical, Inc. (2004).
Wong, 'Rigid mesh fixation for alloplastic cranioplasty,' J. Craniofac. Surg., 5(4):265-9 (1994) Abstract.
Guarda-Nardini, 'Use of porous plyethylene (Medpor) iin maxillofacial surgery, Minerva Stomatol., 44(12):559-82 (1995) Abstract.
Roberson, et al., 'Traumatic cranial defects reconstructed with the HTR-PMI cranioplastic implant,' J. Craniomaxillofac. Trauma, 3(2):8-13 (1997) Abstract.
Lara, et al., 'Technical considerations in the use of polymethylmethacrylate in cranioplasty,' J. Long Term Eff. Med. Implants, 8(1):43-53 (1998) Abstract.
Jones, et al., 'Combined use of titanium mesh and biocompatible osteoconductive polymer in the treatment of full thickness calvarial defects,' Br. J. Oral Maxillofac. Surg., 36(2):143-5 (1998) Abstract.
Temerkhanov, el al., 'The use of titanium mesh plates for graft fixation in mandibular osteoplasty,' Stomatologiia (Mosk), 77(6):31-3 (1998) Abstract.
Moe, el al., 'Resorbably fixation in facial plastic and head and neck reconstructive surgery: an initial report on polyactic acid implants,' Laryngoscope, 111(10):1697-701 (2001) Abstract.
Mouatt, 'Acrylic cranioplasty and axial pattern flap following calvarial and cerebral mass excision in a dog,' Aust. Vet. J., 80(4):211-5 (2002) Abstract.
Liu, James K., M.D., et al., Porous Polyethylene Implant for Cranioplasty and Skull Base Reconstruction. Medscape, Apr. 12, 2004 (Abstract).
The Ahmed Glaucoma Valve, Ahmed website, 2004.
Korean Application No. 10-2005-7019487, Office Action, 6 pages (2 pages of translation), Mar. 30, 2010.
European Application No. 07755661.1, Summons to Attend Oral Proceedings Pursuant to Rule 115 (1) EPC, Feb. 12, 2010.
Janecka, "New Reconstructive Technologies in Skull Base Surgery: Role of Titanium Mesh and Porous Polyethylene," Arch Otolaryngol Head Neck Surg, vol. 126, pp. 396-401, Mar. 2000.
Park, Hun K., Biomechanical properties of high-density polyethylene for pterional prosthesis. http://findarticles.com, Neurological Research, Oct. 2002.
Janecka, IP (2000): New reconstructive technologies in skull base surgery—Role of titanium mesh and porous polyethylene, Archives of Otolaryngology-head & Neck Surgery, 126 (3): 396-401 Mar. 2000.
Oka M., Ushio K., Kumar P., et al. (2000): Artificial Articular Cartilage, Proc Inst Mech Eng [H], 214(1):59-68,2000.

Murakami, N. Saito N., Horiuchi H., et al. (2002): Repair of segmental defects in rabbit humeri with titanium fiber mesh cylinders containing recombinant human bone morphogenetic protein-2 (rhBMP-2) and a synthetic polymer, J Biomed Mat Res, 62(2):169-174, Nov. 2002.

Murakami N., Saito N, Takahashi J., Ota H., et al. (2003): Repair of a proximal femoral bone defect in dogs using a porous surfaced prosthesis in combination with recombinant BMP-2 and a synthetic polymer carrier.

Liu, James K., M.D., et al., Porous Polyethylene Implant for Cranioplasty and Skull Base Reconstruction, Medscape, Apr. 12, 2004.

* cited by examiner

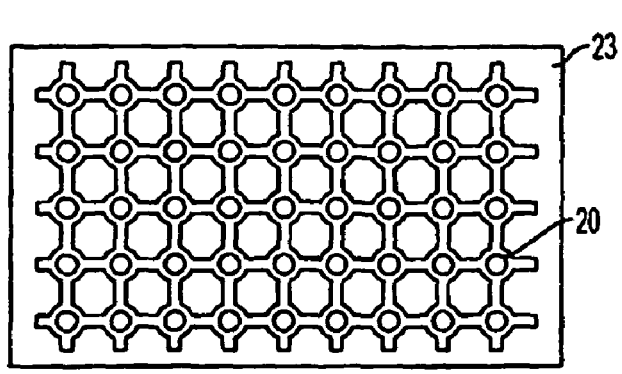
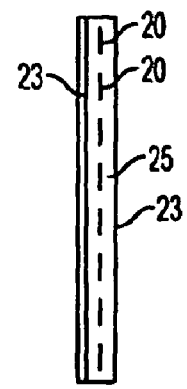
FIG. 1  FIG. 2
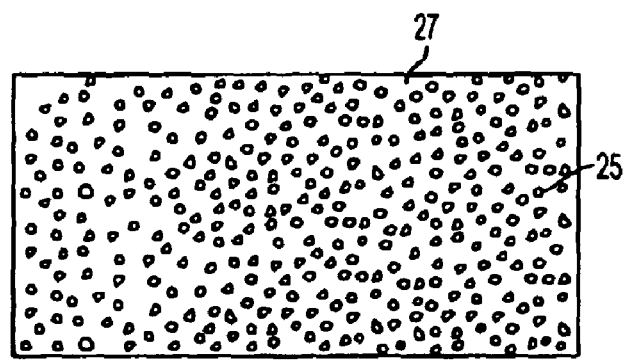
FIG. 3
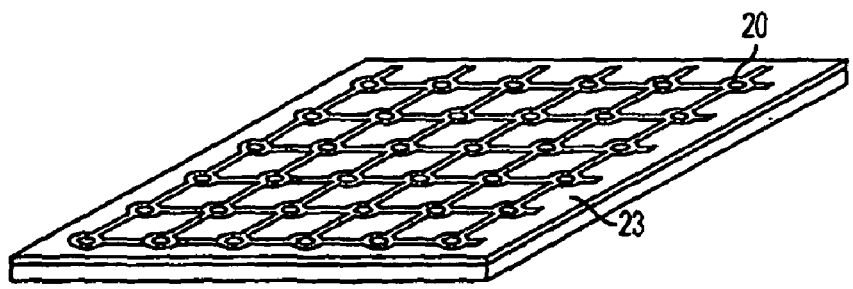
FIG. 4

CRANIOFACIAL IMPLANT

This application is a continuation-in part of U.S. application Ser. No. 10/517,843 titled "Craniofacial Implant" filed on Jul. 12, 2005, now U.S. Pat. No. 7,655,047 which is the national phase application of International Application No. PCT/US2004/011903 filed on Apr. 16, 2004, which claims priority to U.S. Application Nos. 60/463,036 and 60/496,684, filed on Apr. 16, 2003 and Aug. 21, 2003, respectively, the entire contents of each of which are incorporated by reference.

BACKGROUND OF THE INVENTION

Craniofacial and especially orbital wall and floor defects may result from trauma, cancer, resection, or congenital defects. Such defects are typically treated surgically using bone grafts or synthetic implants. Congenital defects or fractures of the complex and relatively thin bone structures surrounding and supporting the human eye present difficult internal bone repair and fixation problems. In instances when the eye is subject to trauma, the margin or rim of the orbit may diffuse the force of the impact. However, compression of the orbital contents sometimes may occur and fracture the relatively fragile orbit floor and/or the lateral and medial orbital walls. Also injury at the lateral orbital rim may produce a fracture within the orbit. When the orbit is fractured standard bone-grafting techniques for orbital reconstruction may not result in predictable eye function and positioning. Often the support of the globe is deficient as a result of under correction of the defect, over correction, or inadequate reconstruction of the orbital volume. Further, the bone graph may be subject to resorption that may result in result in a less than optimal support. The accurate anatomical reconstruction of the bony orbit is essential to maintain normal function and appearance of the eye following orbital fractures. Because most of the bone of the internal orbit surfaces is thin, it is difficult to adequately stabilize the fractured bone fragments without the use of autogenous or alloplastic materials.

Damage to other craniofacial bones and the cranium may also occur from many of the above-listed sources, perhaps trauma and congenital defects being the most common. There are distinct needs to provide implants that can reconstruct these bones to restore and maintain normal function and appearance.

Autologous bone grafts have been considered an optimal treatment method for orbital floor and wall reconstruction, as well as other craniofacial and cranial defects. However, this material is sometimes difficult to obtain and difficult to shape the bone graft material to properly fit within the orbit or other area to be reconstructed. For example, there are problems relating to the tissue donor site morbidity. As discussed above, autogenous bone grafts have frequently been used by craniomaxillofacial surgeons for the reconstruction of the internal orbit. Bone may be harvested from the calvarium and other autogenous materials including iliac bone, split rib bone. Cartilage has also been used as a bone graft material. However, autogenous bones sometimes result in an unacceptable amount of resorption.

Accordingly, it is desirable to provide an improved implant for use in repairing and reconstructing craniofacial and cranial bones, as well as other non-weight bearing bones that may be damaged by trauma or other causes. A variety of alloplastic materials have been used for orbital reconstruction and craniofacial applications including, silicone rubber, Teflon, Supramid, tantalum mesh, Vitallium mesh, titanium mesh, polyethylene, and methyl methacrylate Perforated bio-compatible metallic strips and metallic panels may be used for rigid internal fixation of fractures in trauma surgery and as a plate material for bone immobilization and stabilization. Metal implants can be used for bone graft support material in reconstructive surgery.

Synthetic implant materials have the advantage of no donor site morbidity, ease of use, relative low cost and ready availability. While there are advantages of synthetic implants, some characteristics may be regarded as disadvantages. Silicone rubber has a smooth surface, but does not allow fibrovascular ingrowth into the implant. Further, although it is flexible, it does not readily conform to the profile of the region where it is required or maintain a new shape when shaped to fit a particular location. For example, in connection with the reconstruction of the orbit, a silicone rubber implant is not an attractive option because upon shaping it to the desired profile, it will tend to be biased back to its original shape. While a silicone rubber implant does not maintain its shape, in a case where the soft tissues of the orbit have been traumatized, an implant with a smooth superior surface is desirable to prevent attachment of the tissues to the implant upon healing. Attachment of these tissues to the wall of the implant may result in restriction of movement of the eye, causing diplopia, dizziness, and headaches, as well as a cosmetic anomaly on upgaze, downgaze or lateral gaze.

Implants having a porous structure with predetermined pore sizes allow for fibrovascular ingrowth. In some circumstances, fibrovascular ingrowth is desirable because it integrates the implant within the tissues, and reduces the possibility that that the synthetic material will be rejected. Further, fibrovascular ingrowth on the inferior or sinus side of the implant allows for mucosalization of the implant surface, and since the opposite side of the implant may be a barrier, the sinus is effectively isolated from the soft tissues of the orbit. Similar issues arise in connection with the repair of other craniofacial bones. This arrangement is considered desirable because it increases the ability of the implant to ward off infection and minimizes the chance of a sinus infection from entering through the orbit. Fibrovascular ingrowth is also thought to minimize the chance of implant migration or displacement. However, although use of a material that is flexible and thin (appropriate for orbital floor and wall reconstruction) can be bent to an appropriate shape, the material tends to return to its original shape. Further, using a material that does not have a smooth superior surface, may result in restriction of the orbital tissues due to fibrous ingrowth when used for orbital reconstruction.

Pure titanium is the material of choice in craniofacial reconstructive surgery, especially when the implant is intended to be permanent. As an implant material, pure titanium is preferred because its low density and elastic modules are less than some of the stainless steel or cobalt-chromium alloys that have been used as implant materials. Titanium is corrosion resistant and, when provided in thin sheets, is pliable. Titanium implants many be cut and shaped to the appropriate configuration at the time of surgery. Titanium mesh is easily moldable in situ and easily fixed to bone, but does not have smooth surfaces, nor does it allow for fibrovascular ingrowth. An easily molded material is desirable for use in connection with embodiments of the present invention so that the surgeon can create the correct shape to properly reconstruct the orbital walls or orbital floor. Titanium mesh can be molded to the desired shape by hand and it will retain the shape due to the malleability and strength of the titanium material.

While there are a number of options for an implant material for orbital and other craniofacial reconstruction, there remains a need for a material that is easily moldable by hand and will retain its shape after molding, has a options for surface smoothness or porosity, and is made from highly biocompatible materials. Preferably it is desirable to provide an implant that can be trimmed and bent to shape to fit the shape of the orbital wall or orbital floor reconstruction, and placed in the orbit with the smooth surface on the inside, against the periosteum and soft tissues and with the porous side directed toward the sinus region. Further, it would be desirable to provide a material that can be fixed to the orbital bones with surgical screws or to the surrounding tissues with sutures.

SUMMARY OF THE INVENTION

The present invention is directed to an improved implant and method of reconstruction of craniofacial defects, including cranial defects and orbital defects. Various embodiments of the implant comprise a composite structure comprised of a surgical grade metal provided in a planar or curved sheet form that is encased within a malleable biocompatible material, such as a polyolefin (e.g., polymers and copolymers of the ethylene family of hydrocarbons) like high density polyethylene. The polyolefin may either have a smooth surface or a interconnected open pore structure.

In a first embodiment, one surface of the implant is smooth and impervious so that when the implant is placed within the body, it may form a barrier. In an alternative embodiment of the invention, while one side of the implant has a smooth surface, the opposite side of the implant is comprised of a polyolefin porous surface, such as a porous polyethylene, that allows for fibrous tissue ingrowth. In a further embodiment, both sides of the implant have a polyolefin porous surface, such as a porous polyethylene, which provides an implant with both sides that allow fibrous tissue ingrowth. In one embodiment of a method of reconstruction, the implant is cut and then shaped to conform to the profile of a defect to be treated. The implant is then secured to bony tissue using surgical screws or any other appropriate alternative fastening method. In a particularly preferred embodiment, at least a portion of the implant comprises a mesh, allowing the implant to be malleable, while also maintaining its shape.

Accordingly, the present invention provides a unique implant for the repair of orbital defects, fixation of orbital fractures, repair of other craniofacial and cranial defects.

The present invention further provides a unique composite implant structure which can be shaped for use during a surgical procedures relating to the repair or fixation of the desired bones, and be readily cut, reshaped or bent to conform to the bones to be repaired. In a particular embodiment, the present invention provides an implant that can be used to repair the orbital walls and can be affixed to the orbit or the orbital margin.

In another aspect, the invention provides an implant structure that forms a barrier between the sinus and the soft tissues of the orbit.

In a further aspect, the invention provides an implant that may be used in other applications (such as for other craniofacial and cranial applications or any other applications where bone may need to be repaired or fixed) in which it is desirable to maintain the shape of the implant or form the implant into a desired shape.

Other objects and advantages of the invention will be apparent from the following summary and detailed description of the orbital repair implant structure of the invention taken with the accompanying drawing figures.

BRIEF DESCRIPTION OF THE DRAWINGS

FIG. 1 is a top plan view of a first embodiment of an implant according to the invention wherein top side of the implant is a barrier surface.

FIG. 2 is a side view in elevation of the first embodiment of the invention showing the barrier surface and the bottom porous surface.

FIG. 3 is a bottom view of the first embodiment of the invention.

FIG. 4 is a perspective view of the first embodiment of the invention.

DETAILED DESCRIPTION

Figure 5:
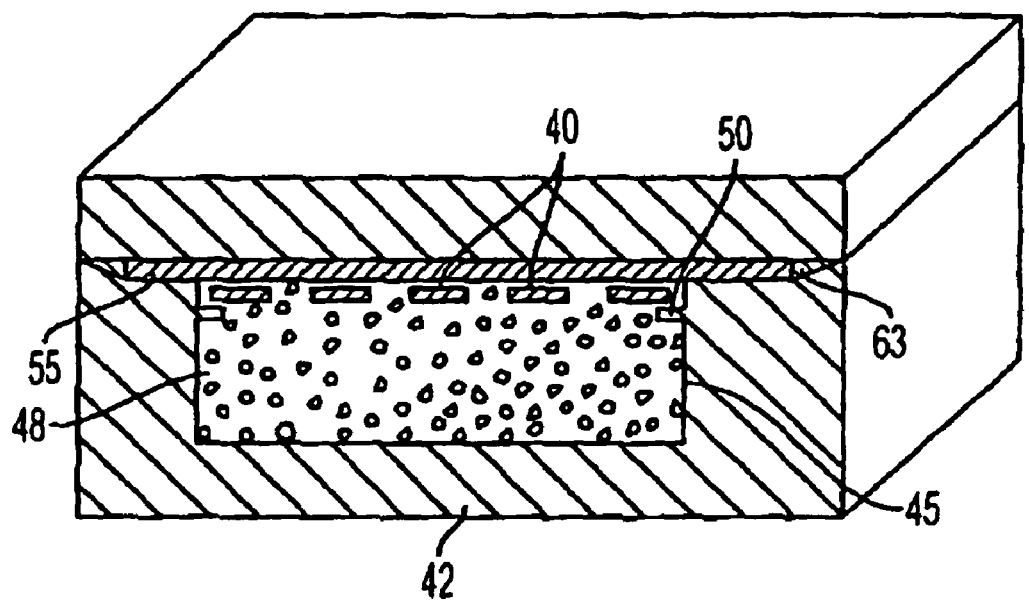
FIG. 5 is a side sectional view of an implant within a mold used to assemble the invention.

The present invention is directed to novel implants for craniofacial surgery, methods for making said implant, and methods of reconstructing orbital and cranial defects with the implants described. As described herein, one preferred application for the implant is for the reconstruction of orbital defects that may have resulted from trauma or disease or birth defects. Other craniofacial and cranial applications are also contemplated. The implants preferably have a mesh portion that is coated or covered with a smooth (or barrier) sheet on both sides of the mesh, a porous sheet on both sides of the mesh, or a smooth (or barrier) sheet on one side of the mesh and a porous sheet on the other side of the mesh.

A first embodiment of the invention comprises a sheet of mesh with a porous layer formed in the interstices of the mesh and at least partially or completely covering the bottom surface of the implant, and a solid sheet of film covering the top side of the implant. This embodiment allows tissue ingrowth on the porous side and prevents tissue ingrowth on the solid film side.

The mesh provides for strength and serves to retain the shape of the implant in a rigid and fixed position. It should be understood that a mesh as used herein may encompass any flat or curved sheet of surgical grade metal that has perforations or passages formed through the sheet. The passages in the sheet help enable the sheet to be shaped or bent in more than one dimension and then retain the desired shape. It is contemplated that the mesh could be formed in a variety of manners including woven screens, etched from plates, formed from solid plates that are cut and then expanded to form a substrate having passages.

The first specific embodiment of the invention is illustrated in FIG. 1 where a solid smooth barrier material 23 lies on top of the mesh material 20 with porous material 25 formed in the interstices and under the mesh 20, and at least partially or completely covering the bottom surface 27 of the implants, as shown in FIGS. 2 and 3. As best seen in FIG. 4, the top surface 23 of the implant preferably has some transparency so that the mesh 20 may be seen through the polyethylene film layer 23. While FIG. 1 shows the mesh extended to the periphery of the implant, it is contemplated that in some embodiments the mesh may not extend to the edge of the implant structure. In yet other embodiments, the mesh may extend from the implant structure. In this later regard, it may be advantageous to extend the mesh from the implant structure to provide for a projection to be employed for the attachment of the implant during the surgical procedure, an option that is described in more detail below. The mesh as described throughout this application is preferably titanium, although other materials are considered within the scope of this invention, non-limiting examples of which are provided below.

Figure 11:
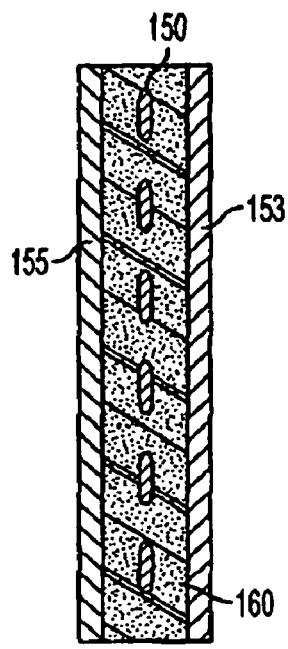
FIG. 11 is a side sectional view of an implant having opposite barrier surfaces that a center section.
Figure 12:
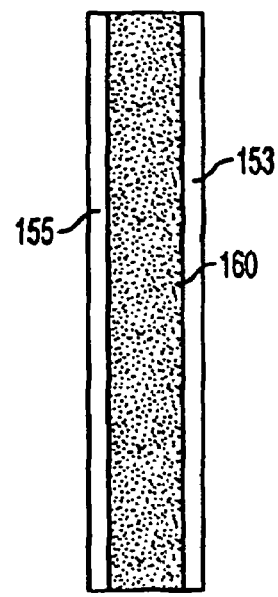
FIG. 12 is a side view in elevation of the implant depicted in FIG. 11.

FIG. 11 depicts yet another embodiment of the invention in which the mesh 150 is placed between two opposite polyethylene barrier sheets 153 and 155. This embodiment prevents tissue ingrowth on both sides of the implant. A porous matrix 160 may optionally be sandwiched between the barrier sheets 153 and 155. The configuration of this implant provides a bendable sheet that has a smooth polyolefin (e.g., polyethylene) surface on both the top and bottom surface. The implant will retain its shape after it has been bent to conform to the contours of defect to be treated. The thickness of the sheets of polyethylene may be selected to result in an implant having the desired thickness, while also retaining the desired malleability or flexibility. In the alternative, the thickness of the implant may be adjusted by variation of the porous matrix layer 160. Like the previous embodiments, the implant may be bent by the surgeon and it will maintain its shape.

Figure 18:
FIG. 18 is a side sectional view of a further embodiment of the invention wherein the metal mesh is formed with an implant with opposite porous surfaces.

In yet a further alternative embodiment of the invention, the structure comprises a mesh plate (preferably titanium, although other materials are considered within the scope of this invention) within a porous matrix (preferably a polyethylene matrix, although other materials are considered within the scope of this invention) wherein all sides have porous surfaces. FIG. 18 depicts a sectional view wherein the mesh 300 is formed with a porous polyethylene matrix. This implant may be suitable for those applications where a smooth barrier surface is not indicated. For example, an implant having porous surfaces that allow for fibrovascular ingrowth on opposite sides may be particularly indicated in cranial applications and for temporal implants for soft tissue replacement, although such implants may be used for any other appropriate procedures or indications.

Temporal implants for soft tissue replacement is intended to refer to implants that may be used to replace the thick temporalis muscle that covers the temporal area of the cranium. This muscle is sometimes used as a pedicled flap to repair soft or hard tissue defects in the craniofacial area. For example, if a tumor is removed from the roof of the mouth, the temporalis muscle may be lifted from the cranium and with one end still attached to its blood and nerve supply. The other end is moved into the defect in the roof of the mouth. This results in a soft tissue defect in the temporal area. Implants according to various embodiments of this invention may be used to fill this defect. (In other words, they are typically attached to the cranial bone, but they do not correct a bony defect, just the temporal soft tissue defect.) In other instances, the temporalis muscle may be cut through when performing a pterional craniotomy, where the cranial bone under the temporalis muscle is temporarily removed to gain access to the brain. Although the bone is replaced, the temporalis muscle will atrophy, resulting in a temporal soft tissue defect. Implants according to various embodiments of this invention may be used in this regard as well.

Figure 16:
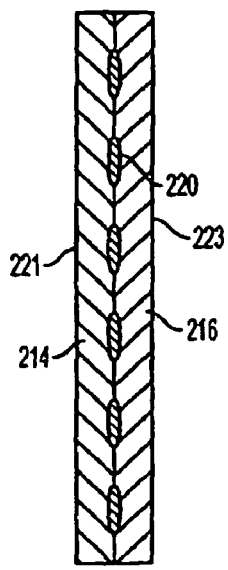
FIG. 16 is yet another embodiment of the invention wherein the implant has opposite barrier surfaces.
Figure 17:
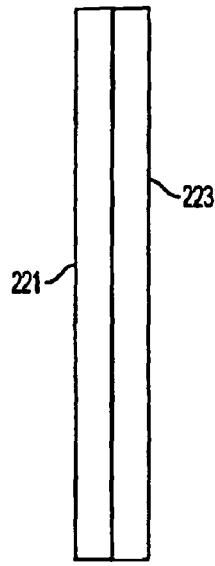
FIG. 17 is a side view in elevation of the implant depicted in FIG. 16.

FIG. 16 depicts yet a further embodiment of the implant wherein the top surface 214 and bottom surface 126 are polyethylene sheets. This embodiment differs from that shown in FIG. 11 because it does not contain an inner porous matrix sandwiched between the sheets. The mesh 220 is contiguous with the internal surfaces of both the top sheet 214 and the lower sheet 216. This implant has a top barrier surface 221 and bottom barrier surface 223 and is indicated in those applications where fibrovascular ingrowth is not desired.

Figure 19:
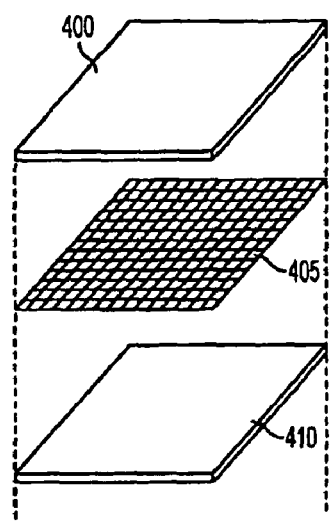
FIG. 19 is an exploded view of an implant having three layers.

FIG. 19 shows an exploded perspective schematic view of one embodiment according to the invention. Top layer 400 may comprise a barrier surface or porous surface. The mesh 405 may be any metallic material suitable for surgical applications that and that is malleable and will retain its shape. Bottom layer 410 may be a barrier surface or a porous surface. This embodiment depicts mesh 405 at the interface between the layers 400 and 410.

In any of the above-described configurations, the mesh is preferably comprised of titanium, although it should be understood that the mesh may comprise surgical grade stainless steel, steel coated with titanium, or titanium nitride, or titanium alloyed with other metals, to adjust the physical properties of the metal as needed for the particular applications, composites of any of the above materials, or any other appropriate material that will allow the implant to be at least partially pliable, while also maintaining its structural integrity.

In another embodiment of the invention, it may be desirable to impart shape memory to the implant by using a metal that returns to its shape when bent. For instance, in endoscopic procedures to repair an orbital floor defect, a thin sheet implant, cut slightly larger than the defect, may be pushed through the defect from the maxillary sinus side. Using a flexible but springy sheet would allow the implant to return to is preformed shape after flexing it enough to push it through the defect, thus allowing the surgeon to repair the defect from the maxillary sinus without entering the orbit from outside the body. In the current state of the art, this is accomplished with porous or solid polymer sheet, but using a metal mesh with shape memory characteristics could allow for larger, stronger, or thinner implants for this purpose.

The metal component of the invention could comprise wire screen, expanded metal, perforated metal sheet, perforated bars, an interconnected meshwork of perforated bars, a three dimensional grid, including rectangular, square triangular, or any appropriate cross section of grid design, a free form solid, a perforated or machined shaped sheet, or any combination thereof. The metal component may have openings ranging from none to large free form openings. The metal surfaces may be smooth or irregular, including irregular surfaces which improve the attachment of the polymer component to the metal component. (As described above, any of the metal components described here may be enveloped in porous polymer, porous polymer with one or more barrier surfaces, or with solid smooth polymer.) Methods for fabricating the metal component include, but are not limited to, machining from stock metal, acid etching, EDM (electrode deposition machining), laser cutting, water jet machining, selective laser sintering, perforating and expanding metal sheet, or any other method known to the art.

In a particular embodiment of the invention, the metal components may be designed to support load bearing structures in the body, such as in the mandible or in long bone fracture repair. The polymer component provides a smoother, lighter, void filling material which allows vascularization by the body's tissue. For example, when full thickness portions of the mandible are resected to remove a tumor, the mandible is often reconstructed by bridging the gap with a load bearing metal fixation plate.

Previously-used plates are typically 2 mm thick, 9 mm tall, long enough to bridge the defect, with evenly spaced holes to accept screws to allow fixation to the remaining portions of the mandible, but without a polymer cover. These plates are subject to erosion through the surrounding or overlying tissues. Furthermore, they do not fill the void left by the resected bone, leaving a void in the tissues. By embedding a fixation plate of this type in a polymer structure (such as a high density polyethylene), the resulting implant can be shaped to fill the bony defect, and can be made with a smoother surface that tapers gently to the remaining bone, reducing the probability that the plate will erode through the surrounding tissues. The polymer component of the implant can be made to allow the polymer to be carved in the operating room to the appropriate size and shape to fit the defect created by the resection procedure. The metal portion provides the necessary load bearing property to effect a permanent repair, while the polymer portion restores natural contour to the skeleton.

In a preferred embodiment, the porous layer is comprised of a polyolefin and even more preferably, a high density polyethylene that either has an interconnected pore structure (referred to as "porous") or a smooth non-porous structure (referred to as "smooth"). One potential polyethylene is ultra high molecular weight polyethylene (UHMWPE). Alternatively, the layer may comprise polyether ether ketone (PEEK), polyethylene terephthalate (PETE), nylon, polypropylene, or any polymer of aliphatic hydrocarbons containing one or more double bonds, composites of any of the above materials, or any other appropriate material that can be bent or otherwise formed to cover the mesh, and allow the implant to be at least partially pliable, while also imparting the desired porosity.

Figure 13:
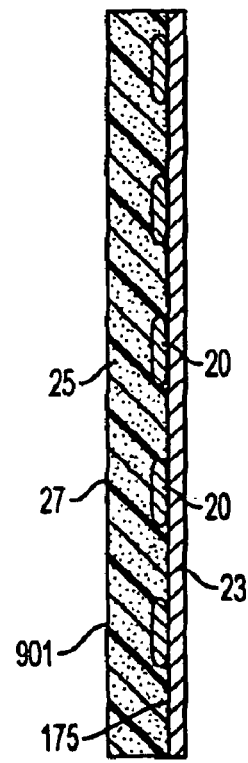
FIG. 13 is a side sectional view of the implant depicted in FIGS. 1-3.

Now referring to FIG. 13, a side sectional view of the implant depicted in FIGS. 1-4 shows the mesh 20 formed along the interface 175 between the porous layer and the solid polyethylene layer 23.

Figure 21:
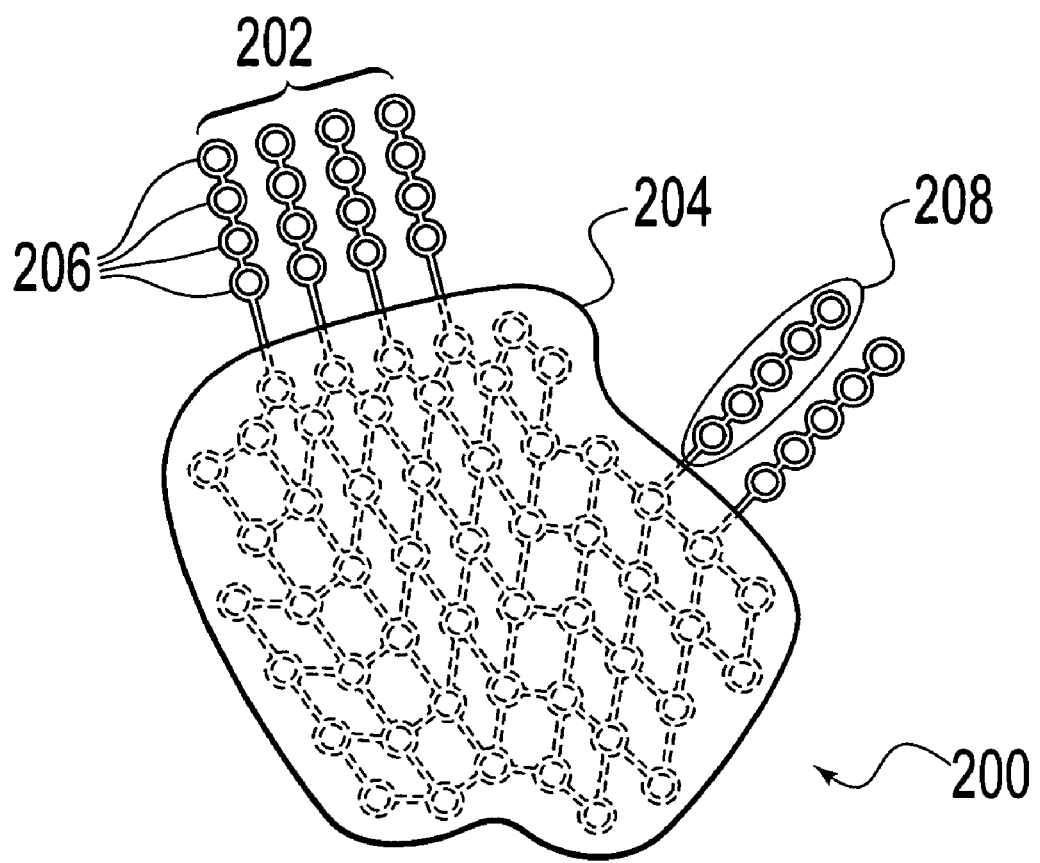
FIG. 21 is a top plan view of one embodiment of an orbital reconstruction implant with attachment structures.

One example of this embodiment is shown in FIG. 21, which shows an orbital implant 200 having attachment structures 202 extending from the periphery 204 of implant 200. In this embodiment, attachment structures 202 are shown as a series of four circular rings 206, although it should be understood that attachment structures 202 may take on any form that allows them to receive any appropriate fixation device (such as a screw, a tack, a pin, a surgical nail, and so forth). For example, attachment structures may be square or rectangular shaped, oblong, triangular, trapezoidal, or any other appropriate shape. They may also be provided in any number, such as one, two, three, four, ten, twenty, or any other desired number. They may also be any length that is appropriate for the site of insertion and the degree of attachment required.

Additionally, although attachment structures 202 are shown in groups of multiple strands 208 (i.e., one group of four strands and another group of two strands, the term "strands" being used to refer to a strip of the structures), it should be understood that structures 202 may provided in any number of strands 208 and in any configuration or combination. For example, a single implant could have a single strand of rings in one place, a triple strand of squares in another place, and/or evenly spaced strands in other places. In other words, one or multiple strands having one or multiple shapes (in any combination) may extend from implant 200 in groups, in strategically placed locations, or randomly along the periphery 204. It should be understood that providing multiple attachment structures 202 provides the surgeon with more location options for securing implant 200 in place.

Attachment structures 202 may be placed in certain areas where it is envisioned that attachment may optimally take place. Any attachment structures 202 that are not used may optionally be trimmed or clipped from implant 200 to prevent them from interfering with the surgical site and/or the healing process. The attachment structures 202 described in this section may be used in connection with any of the implant embodiments described herein.

While in the embodiments depicted herein, the mesh is depicted in the center of the implant structure, it is contemplated that the mesh may be positioned adjacent to the top thin sheet layer or other locations within the implant depending on the respective application.

Now referring to FIG. 5, to manufacture the implant as depicted in FIG. 1, a mesh 40 is selected and positioned on tabs 50 that project from the sidewalls 45 and 48 of the bottom of the mold section 42. Next, polyethylene fines are introduced into the mold so that they fill the void below the mesh 40, the spaces between the titanium mesh 40 and cover the top surface of mesh 40. Last, a thin sheet or continuous film of solid polyethylene 55 is placed on the top of a suitable mold. The solid barrier sheet 55 extends beyond the edges of the cavity section of the mold and extends to the mold surface 63 thereby maintaining the sheet on one side of the mold.

FIG. 5 is a sectional view of the implant according to the invention located within a mold. As depicted therein, the mesh is located adjacent to the barrier layer on the top of the mold. The barrier layer is formed of a solid sheet of polyethylene and the porous section is made by sintering together polyethylene fines under heat and pressure. The solid sheet may be made by introducing polyethylene fines to a press having opposite smooth metal sheets and heating the surfaces causing the fines to completely fuse together. When the implant has cooled, the structure may be removed from the mold because both the tabs 50 and the implant material have some flexibility.

An alternative method for manufacturing various implants is to coin curves into the implant for improved anatomic shapes. This is particularly useful because it is easier to make the composite implants described herein as a flat sheet of material rather than manufacture it as a curved design. However, there are many procedures for which the implant should be preferably pre-curved or pre-shaped so that it more accurately fits the bone to be replaced. Even though the implants are malleable by hand, it is still useful to provide implants that are pre-shaped. This can help reduce operating room time, because the implant is already generally shaped appropriately.

For example, a cranial implant may be provided with a rounded or dome shape so that it fits the cranium more precisely. An orbital implant may have a pattern that mimics the orbital floor or any other anatomical feature. The coning process generally entails taking a flat manufactured implant (metal mesh embedded in an polyolefin layer) and coining the desired shape into it by putting the implant into a mold, applying pressure so that the mold causes the implant to bend in the mold's shape. A heat cycle allows the polyolefin (e.g., polyethylene layers) to relax and bend into the desired shape.

Figure 6:
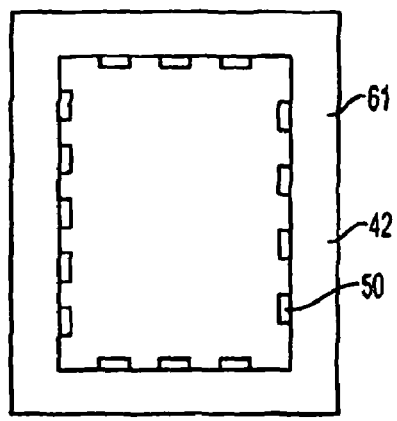
FIG. 6. is a top view of a mold depicted in FIG. 5 with the top cover removed.
Figure 7:
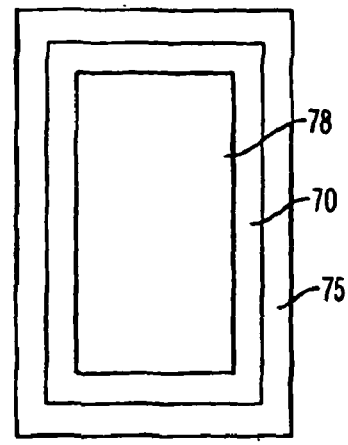
FIG. 7 is a top view of an alternative mold that can be used to create the invention with the top cover removed.

Now referring to FIG. 6, a contemplated arrangement depicting a plurality of tabs 50 provided on the lower section of mold 61 is shown. The mesh sheet will rest on or is supported by the tabs 50 provided around the periphery of the mold. The tabs are placed a distance from the top surface of the mold that is slightly less than the width of the mesh, so that when the top of the mold that retains the barrier sheet is placed over the mold bottom, the thin barrier sheet may come into contact with the mesh. FIG. 7 depicts an alternative arrangement wherein the mold is provided with a shelf to retain the mesh in position near the top of the mold.

Figure 8:
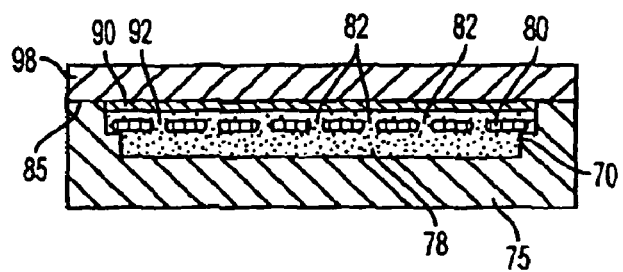
FIG. 8 is a side sectional view of the mold depicted in FIG. 7

FIG. 7 depicts an alternative arrangement for a mold wherein the mesh may be received on a shelf 70 that is suspended over the cavity using a shelf 70 around the mold cavity that holds the mesh sheet in position. As best seen in FIG. 8, shelf region 70 that extends into the void area 78 of mold 75 supports the edges of the mesh. A polyethylene sheet 90 is positioned above polyethylene fines 92 that fill the cavity 78. The passages through the mesh are identified by reference number 52. It should be understood that the dimensions, including the depth of the cavity from top surface 85 of bottom mold section 75, and the length and width of the mold may be altered depending on the particular application intended for the implant.

As illustrated by FIG. 8, the fines 92 come into contact with both the smooth polyethylene sheet 90 and the mesh 80. Once the mold is filled as described above, the top section 98 is placed over the components and the materials are subjected to heat and pressure, as is known in the current art, to form a porous polyethylene material. The heat and pressure cause the fines to be sintered together and to affix the polyethylene sheet and titanium mesh. The resulting structure has titanium mesh embedded within a porous matrix and a solid smooth polyethylene film that is attached both to the titanium mesh and/or to the porous polyethylene structure. The sheet or film of polyethylene is impervious to water and serves as a barrier.

In a preferred embodiment of the invention described above, the polyethylene film is approximately 0.1 mm thick, the titanium mesh is approximately 0.35 mm thick and the porous polyethylene is approximately 0.9 mm thick, inclusive of the imbedded titanium mesh. Thus the overall thickness of the material is approximately 1 mm. In another preferred embodiment the titanium is 0.35-1 mm thick, the polymer is 4-6 mm thick (this embodiment may be particularly useful for certain cranial repairs). In yet another embodiment the titanium is 1-3 mm thick, with polymer being 3-5 mm thick (this embodiment may be particularly useful for mandibular reconstruction).

In another embodiment of the invention, the titanium component rests at one surface of the porous or porous/barrier polymer component, to allow the metal component to rest securely against the bone, for better stabilization of the bone against the metal component which is screwed to the bone.

Also, for implants that may be used in non-load bearing situations, the polymer portion of any of the above embodiments of the implant can be fixed to the bone with screws which go through the polymer only, without using the metal component for implant fixation.

Figure 9:
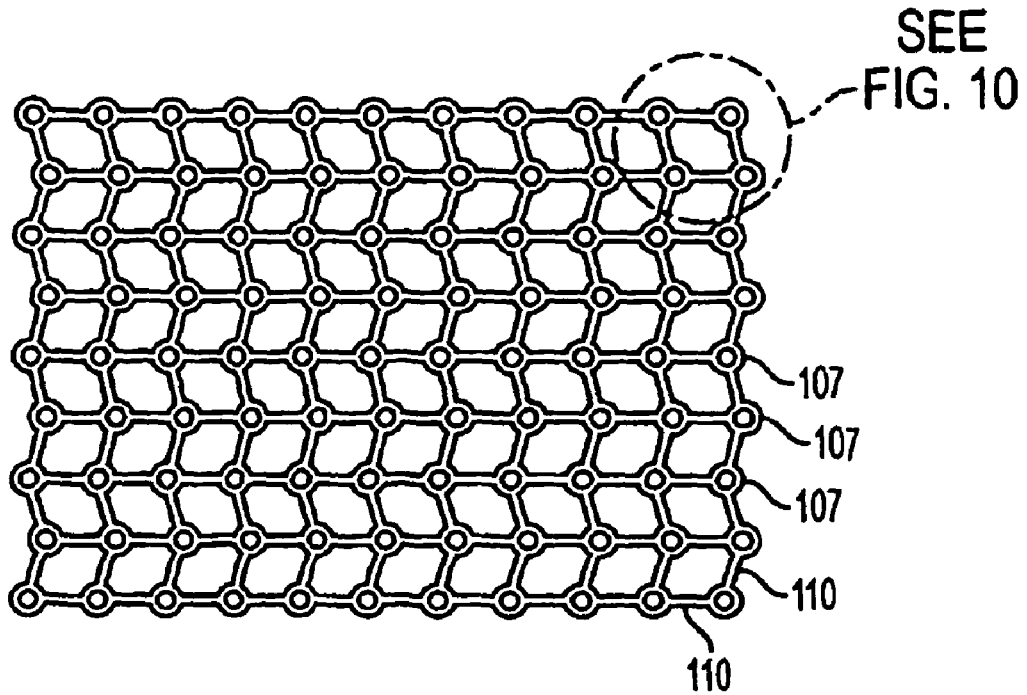
FIG. 9 is a top view of titanium mesh that may be employed with any of the embodiments of the invention.
Figure 10:
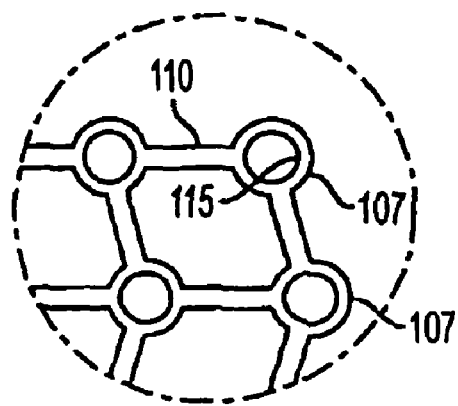
FIG. 10 is an enlarged view of a section of the titanium mesh depicted in FIG. 9.

Now referring to FIG. 9, in a preferred embodiment of the invention, the titanium mesh consists of a series of annular rings 107 that are attached to adjacent annular rings by bridges 110 also made of titanium. As best seen in FIG. 10, the annular rings have countersunk holes 115 that will receive the head of surgical screw. This structure allows for flexibility of the titanium component within the implant and the countersunk holes allow for easy fixation of the implant to the bone using appropriately sized surgical screws. In the preferred embodiment of the invention, the titanium is of sufficient strength in relation to the thickness of the polyethylene components (the solid sheet and the porous matrix) so that the implant will hold its shape after being bent by the surgeon. It is therefore contemplated that during a surgical procedure the surgeon may bend the implant to conform to the shape of the defect that is being treated. In a preferred embodiment the surgeon can bend the implant by hand during the procedure. The implant as described above can also be cut with conventional plate cutters that are routinely used for cutting titanium surgical plates or mesh.

The implant may be fixed to the bony defect with typical craniofacial screws that are sunk through the polymer portion and into the bone in lag screw fashion, sunk through one of the holes in the metal component, or sunk through a new hole drilled in the metal plate component by the surgeon. The polymer component may be designed to be pliable enough that the screw head can be driven flush with the surface of the polymer covering the metal component. The implant can also be fixed with conventional craniofacial plates and screws, where the plate overlaps the junction between the bone and the implant, and screws on the implant side are screwed through the plate hole and into the polymer portion of the implant, whereas screws on the bone side are screwed through a plate hole and into the bone.

The implant may additionally or alternatively be fixed with wires, looped through the metal in the implant and through drill holes in the bone, which is an older technique generally known to craniofacial surgeons. It could be fixed by inserting an extended metal arm from the implant edge into the cancellous space of cranial bone, with or without subsequent fixation with screws, nails or tacks. The polymer component can additionally or alternatively be sutured to the periosteum, using permanent suture. If provided, a plate extending out of the side of the implant can be bent up to the top of the edge of the bony defect, and then over the bone at the edge of the defect and then screwed, nailed, tacked or riveted into place.

While preferred embodiments of the titanium mesh are illustrated by FIGS. 9 and 10, other titanium mesh products that can be used in connection with the invention are commercially available from sources that include Stryker Instruments, Synthes Maxillofacial, Leibinger, KLS-Martin, L. P. and Walter-Lorenz Surgical.

Figure 14:
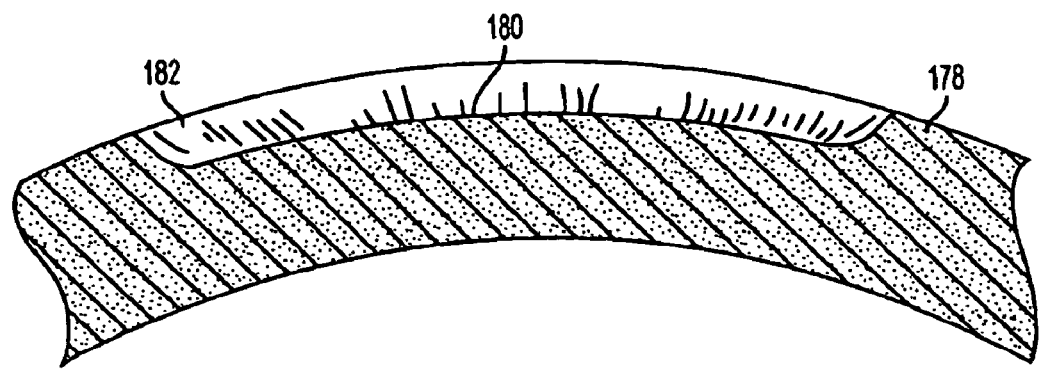
FIG. 14 depicts a sectional view of a cranial defect.

As seen in FIG. 14, a defect in the cranium 178 has a floor 180 and a wall 182. This defect is typically called a split calvarial defect, where only the outer cortical surface is removed from the cranium. Split calvarial grafts are taken to repair craniofacial defects, and the resulting defect is usually under the hair and often is not repaired.

In order to address this defect, the implant may be bent to conform to the contour of the defect and cut to the shape of the defect. (It is possible to provide the implant in various sizes, which can help reduce waste and time, by reducing the amount of materials that is required to be cut). The implant is placed within the defect and one side, for example, a bottom porous layer, is brought into contact with the bone on the floor and sidewalls. The implant may be secured into place with screws or sutures. Any of the embodiments of the implants described may be used for this procedure, although an implant having at least one porous surface to encourage tissue in-growth (e.g., of the bone) is particularly preferable. If an implant with one or more of the bottom surface, the top surface, and/or the sidewalls are porous, fibrovascular ingrowth into the implant is encouraged and this ingrowth serves to further stabilize the implant and diminish the possibility of rejection. It may also be preferable to use an implant that also has at least one smooth barrier surface to prevent the dermis from attaching to the outer surface of the implant.

Figure 14A:
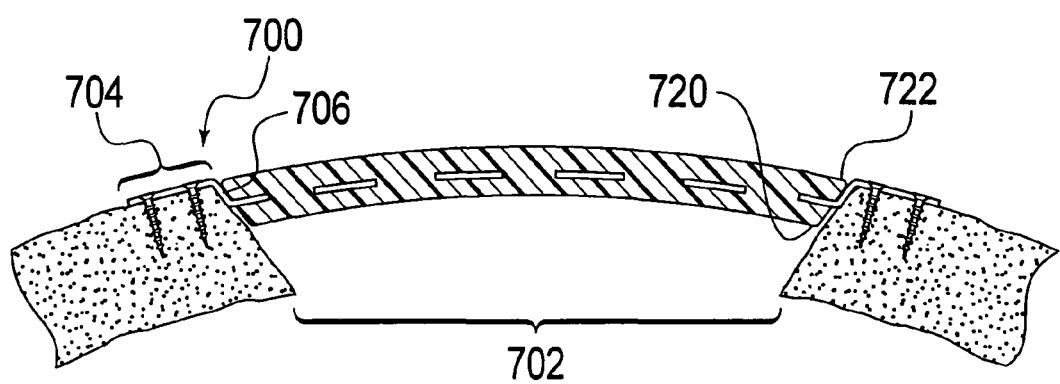
FIG. 14A depicts a cranial defect with one embodiment of a cranial implant in place.

As shown in FIG. 14A, the implant may optionally have an attachment structure or bracket 700 that extends from the implant. This bracket option is particularly useful in connection with a cranial implant designed to repair a bone defect or missing bone portion in the skull. Because the bone defect or removed bone often leaves an indentation portion 702 and because the implant cannot be secured to the exposed dura matter of other soft tissue, brackets 700 may extend from implant, either from the lower edge surface 720 of implant, the upper edge surface 722 of implant, or somewhere in between 744. The brackets may be added to a completed implant or they may be formed integrally with the mesh during manufacturing. In a preferred embodiment, the brackets may have an attachment portion 704 and an angled portion 706. The attachment portion may be similar to any of the attachment portions described above. The angled portion 706 extends from the implant and allows the implant to extend down into the cavity of missing bone, and then angles up so that the implant can still be attached to the bone surrounding the cavity. If desired, the brackets 700 can be manufactured so that they are bendable (with an appropriate amount of force) and cuttable to be shortened if need be.

Figure 15:
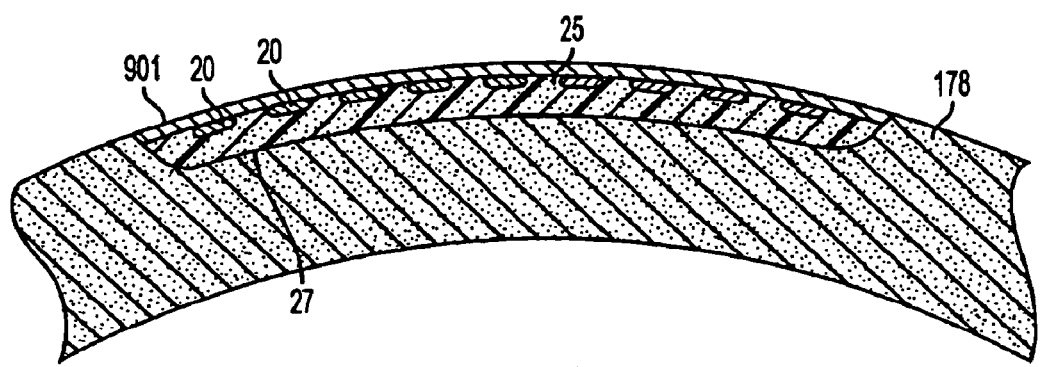
FIG. 15 is a side sectional view of the implant shown in FIGS. 1-3 within a cranial defect.

FIG. 15 illustrates an example where a barrier was used on the top of the implant. This might may be used to help induce bony ingrowth into the underside of the porous implant, by excluding soft tissue ingrowth from the overlying tissues. The smooth barrier surface 901 on the implant allows the skin to slide over the implant area.

Figure 22:
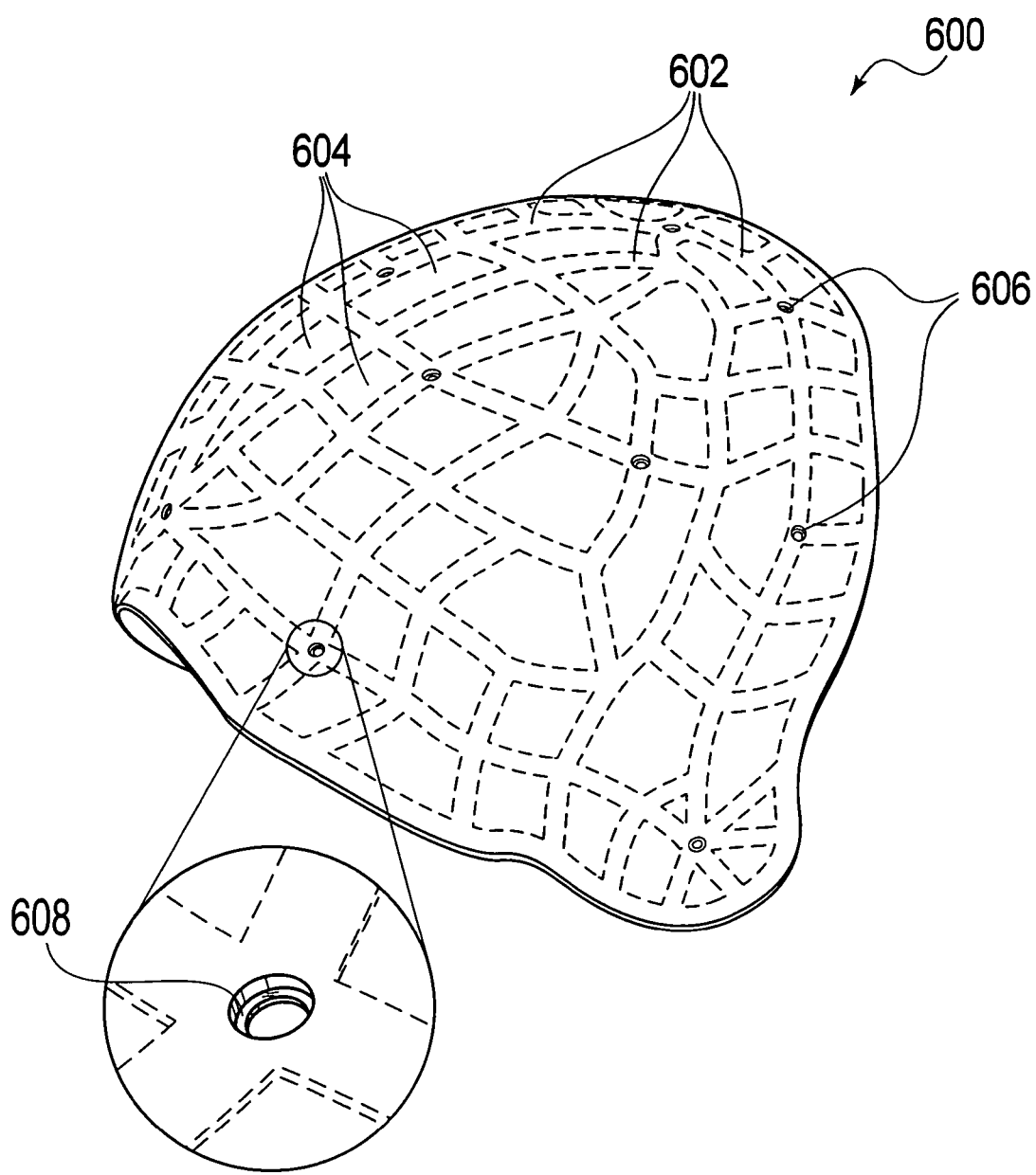
FIG. 22 is a top plan view of a cranial implant made according to certain embodiments of the invention.

Another embodiment of a cranial implant is shown in FIG. 22. This implant 600 is comprised of a series of mesh bridges 602 that are connected at various angles to form variously sized inner areas 604. Mesh bridges 602 and inner areas 604 may be any appropriate size that will provide the desired strength. (This embodiment omits the annular ring structures of FIGS. 9 and 10, which can help add strength to the implant 600, although in some instances, it can lower its malleability. It should be understood, however, that annular rings may be used with cranial implants if desired.) The mesh portion is preferably covered by an upper layer and a lower layer of material, each layer of which may be a solid, non-porous barrier sheet, a porous layer, or any combination thereof. An optional layer of material may also be sandwiched between the upper and lower layers (as described above in connection with FIG. 11), in order to add thickness, support, and/or to allow the mesh to be completed enclosed by material.

As shown in FIG. 22, one embodiment of a cranial implant may have a series of one or more openings 606 that are adapted to receive a fixation structure for securing implant 600 in place. In certain embodiments, the openings may be lined with reinforcing features. They may also have a ringed portion where the upper and/or lower layer is removed to reveal a slight portion of a mesh ring 608, so that the fixation device can be countersunk into the implant 600 and not protrude above the layers.

Figure 23:
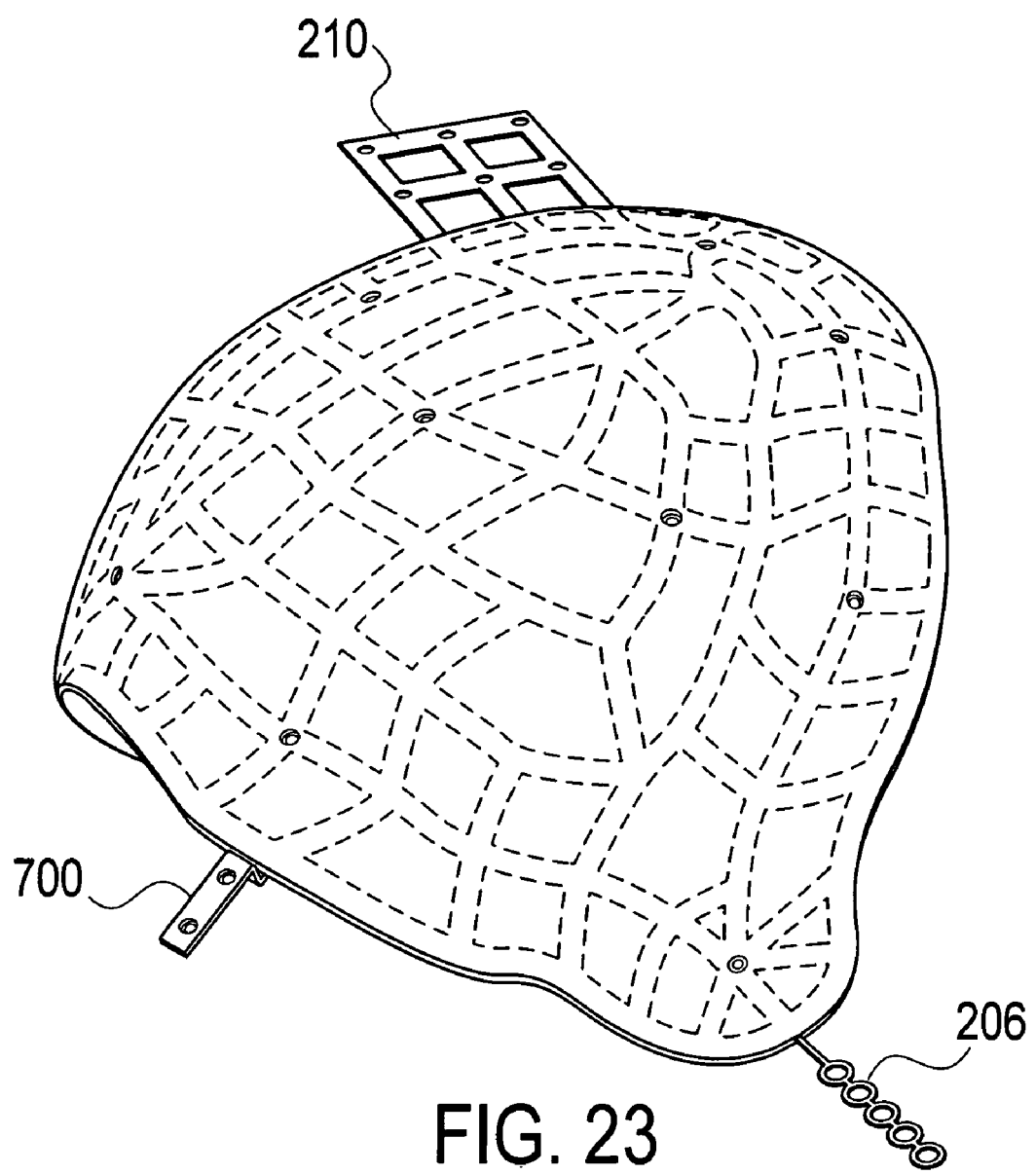
FIG. 23 shows an implant with a series of alternate attachment structures.

FIG. 23 shows an alternate embodiment of a cranial implant. This embodiment shows optional attachment structures 202 extending from the periphery of implant 600. As shown, the attachment structures may be a portion of the mesh 210 that has been extended past the polyolefin layer, they may be brackets 700 (as discussed above in connection with FIG. 14A), they may be ringed structures 206 (as discussed above in connection with FIG. 21), or any combination. FIG. 23 shows many options on a single implant, which is one embodiment, although another option is to provide attachment structures that are of the same type at multiple locations on a single implant.

Figure 24:
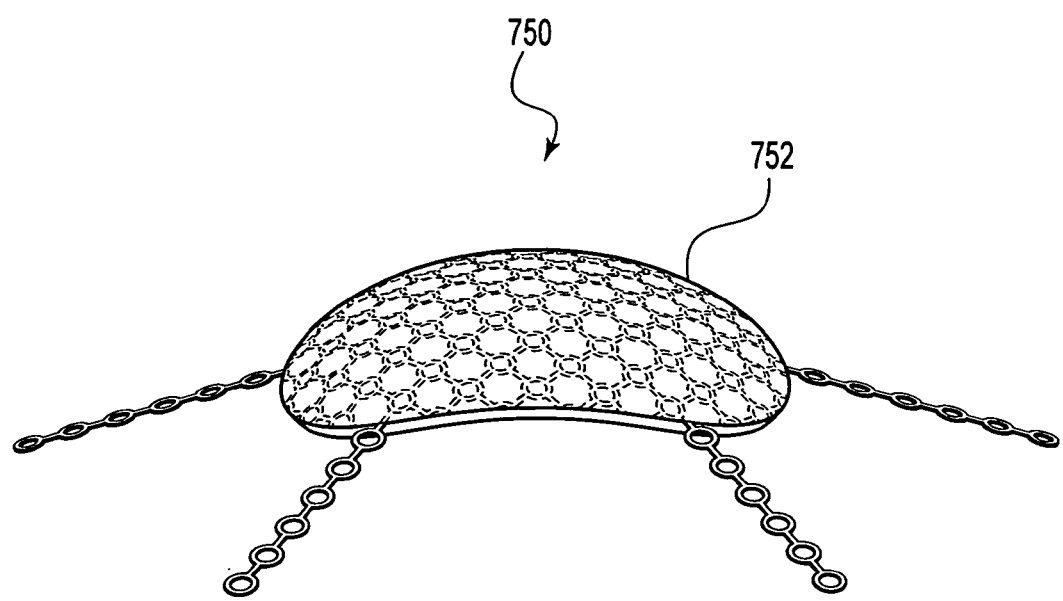
FIG. 24 shows a burr hole cover embodiment.

FIG. 24 shows an example of a burr cover 750. During brain surgery, for example, a portion of bone may be removed by drilling four burr holes in a square or rectangle and then using a thin saw to connect the holes and remove the desired bone. Once the surgery or procedure has been competed, the removed bone may be replaced, but there are still four (or more, depending on the shape of bone removed) small empty burr holes that need to be filled. Accordingly, one embodiment of the present implant may be shaped in a generally circular configuration with various forms of any of the attachment structures 202 described herein extending from the periphery 752 of burr hold cover 750. In a particularly preferred cover 750, there are six or more attachment structures, providing the surgeon with options and then being removable once the attachment structures to be used are chosen. It is also preferred that the burr hole cover 750 have a slight amount of curvature.

Various implants according to alternate embodiments of the invention may be used to cover any portion of the cranium, such as the frontal, occipital, parietal and temporal bones, portions thereof or combinations thereof. The implants may also be used to repair other bones of the face, such as the maxilla and mandible. One option is to provide implants with openings that are sized and positioned to account for various nerves and blood vessels that would otherwise be pinned beneath the implant in use, which will be described in more detail below.

In the preferred embodiments of the invention described above, the pore size of the porous polyethylene is sized large enough to allow for fibrovascular ingrowth. This pore size range would preferably be in the range of 1-1000 microns, and even more specifically, 100-250 microns, and even more specifically could vary in the range of 20-500 microns. As previously discussed, while polyethylene sheets and high density porous polyethylene matrix are preferred, it is also contemplated that other synthetic resins and combinations can be used in connection with the invention. For example PETE, PTFE and/or nylon may be selected as the thermoplastic resin. It is also should be understood that the Figures depicted herein are not necessarily drawn to scale. For example, the barrier in FIGS. 1-4 may be formed with a sheet having a much smaller width than the drawings may suggest. In a preferred embodiment the invention as depicted in FIGS. 1-4 is approximately 5 mm wide by 10 mm in length and has a thickness of approximately 1 mm. However, other dimensions are contemplated, including but not limited to 10×100 mm, 100×100 mm, 20×200 mm, or 5×5 mm.

Figure 20:
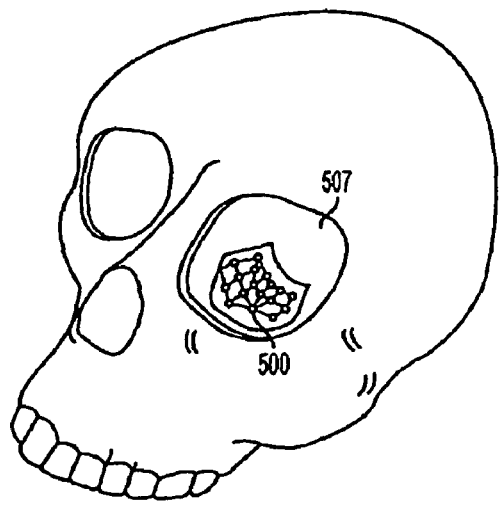
FIG. 20 is a perspective illustration of an implant according to the invention shown in an orbital reconstruction application.

FIG. 20 depicts an implant 500 made according to the invention in position on the orbit floor of an orbit 507. Although shown in connection with the inferior orbital floor, it should be understood that any of the embodiments of the implants described herein may be used for all aspects of the bony orbit, such as the frontal bone, the greater wing of the sphenoid bone, the zygomatic bone or arch, the maxillary bone, the lacrimal bone, and/or the ethmoid bone. The implants may also be shaped specifically for use with a particular area of the face or cranium. They can be curved, planar, or in most cases, malleable to be molded and/or twisted to the desired shape. Depending upon where the implant is to be used, it may be shaped for use with a particular area of the face or cranium. In a particular embodiment, the implants are provided in a kit of multiple implants (e.g., an orbital kit, a cranial kit, etc.) having various shapes and features to provide the surgeon with a number of alternatives depending upon the patient size and the area of the damaged bone.

The implants may further include openings (foramina), grooves, and/or channels that are intended to permit the transmission of a nerve such as the optic nerve, ophthalmic nerve ortrochlear nerve, a duct such as the nasolacrimal duct, or one or more blood vessels. A channel may also be used to drain a site of excess fluid, such as blood, or sample fluid, such as cerebrospinal fluid for analysis. In other words, providing such openings, grooves, and or channels in desired locations on various embodiments of the implant might allow the implant to be used over a nerve without causing any impingement (or crush) of the nerve when the implant is secured in place.

Another option is to provide implants that have attachment sites in various locations that are specific to the area where the implant is to be used. For example, the attachment structures 202 shown in FIG. 21 are one option, and their location and type can be varied from implant to implant. Examples of attachment sites that may be specifically designed for are certain muscle origins/insertions, tendons, artificial structures (such as a nose, and ear, and so forth).

In specific embodiments, the implants may be shaped to be thicker in some areas than others, for example, they help provide a similar appearance to both sides of the head or face due to bone loss or deterioration or more damage to one side than the other. In one instance, the polyethylene thickness could be increased for various types of implants and provided in a kit to provide the surgeon with a range of options. It may also be possible to stack implants (e.g., attach one or more implants on top of each other) to create a more even appearance to the surgical site once closed. It is also possible to provide implants of greater strength and protection, such as for the mastoid process of the temporal bone, the petrous part of the temporal bone, and so forth.

Kits may also be provided. For example, a kit with various components for a facial or a cranial kit may include the different shapes, different fastening means (e.g., screws, pins, etc.), different attachment lengths, different thicknesses, and so forth of the same item. The kit could also include aids to shaping the implant such as a clear template of the implant shape upon which the surgeon would trace the defect, cut it out of the clear plastic template, and transfer the defect shape to the implant before cutting the implant to size. The kit may optionally further include scissors for cutting the template and/or trimming the implant and instructions for the use of the implant system. Variously sized implants may also be provided.

It is further possible to provide implants having mesh with various thicknesses and patterns throughout, which allows the implant to be more malleable in some places than in others. For example, some implants may include a combination or annular ringed areas (e.g., as shown in FIG. 9) and areas with bridges only (e.g., as shown in FIG. 22). This can impart various degrees of strength and rigidity to some areas, while imparting other degrees of malleability and moldability to other areas on the same implant. Additionally or alternatively, one portion of the implant could provide double bridges, thicker bridge, or bridges that are closer together, or any other appropriate configuration that allows varying degrees of strength and malleability.

A further optional feature is to custom-design an implant for a particular patient. A mold may be used to create a certain shape for a certain patient and the implant can be designed in a custom manner. Another option is to provide molds as a part of a kit, which would give the surgeon a general mold to initially form the implant, but then allow the surgeon to further fine-tune the implant to fit the patient being treated.

Another optional feature that any of the implants described herein may have is to be seeded with the autologous or heterologous cells (e.g., stem cells, osteoblasts, fibroblasts). Biologically active molecules such as growth factors, hormones, antibiotics, and/or with any other biological substance may be applied to the implant in order to either help prevent rejection of the implant, facilitate cellular growth into the implant, help stimulate capillary formation, and so forth. The cells or hormones or other substance may be applied topically to the implant prior to implantation, the implant could be soaked in a solution containing the biologically active molecule and or cells, the material could be sprayed on, applied by syringe, the material may be dissolved in a slow release resorbable polymer, which is then formed into the pores of the implant, or by using any other appropriate application method.

In addition to the repair and reconstruction of orbital defects, the implants according to the invention may be advantageously employed with other surgery such as the repair of lost bone flaps resulting from neurological procedures, repair of the mastoid area after a mastoidectomy, fixation for LeFort procedures, fixation for sliding genioplasty. It is further contemplated that the planar sheets may be bent into tubular shapes and used for orthopedic applications. A planar sheet bent in a U shaped configuration may be useful in connection with spinal fixation procedures or the repair of herniated disks.

The invention having been described in detail with respect to preferred embodiments above, it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A surgical implant for bone repair comprising a first surface and a second surface, the implant comprising a porous thermoplastic matrix having an interconnected pore structure throughout the matrix, and a surgical grade metal mesh embedded within the porous thermoplastic matrix such that the matrix encases the mesh and fills interstices of the mesh, and wherein the implant is bendable or displaceable by manipulation by hand, wherein upon the displacement of the implant, the implant will generally maintain the shape to which it has been bent or displaced in a rigid and fixed position for attachment to bone, wherein the mesh provides a structure for attachment to bone.

2. The implant recited in claim 1, wherein the metal comprises titanium, surgical grade stainless steel, steel coated with titanium, titanium nitride, titanium alloyed with other metals, composites of any of the above materials, or any combination thereof.

3. The implant recited in claim 1, wherein the thermoplastic matrix comprises polyethylene, high density polyethylene, ultra high molecular weight polyethylene, polyether ether ketone, thermoplastic resins, polyethylene terephthalate, nylon, polypropylene, polyolefin, any polymer of aliphatic hydrocarbons containing one or more double bonds, composites of any of the above materials, or any combination thereof.

4. The implant recited in claim 1, wherein the first surface, the second surface, or both surfaces comprise a non-porous barrier layer surface.

5. The implant recited in claim 1, wherein the first surface, the second surface, or both surfaces comprise a porous surface having pores sized to allow fibrovascular ingrowth into the porous thermoplastic matrix.

6. The implant recited in claim 5, wherein pore sizes range from about 20 to about 500 microns.

7. The implant recited in claim 1, wherein one of the first or second surfaces comprises a non-porous barrier layer surface and the other of the first or second surfaces comprises a porous surface.

8. The implant recited in claim 1, further comprising one or more attachment structures adapted to attach the implant to a desired surface.

9. The implant as recited in claim 8, wherein the one or more attachment structures comprise openings in the implant and through the mesh that will receive and engage the head of a surgical screw or surgical bone anchor.

10. The implant as recited in claim 8, wherein the one or more attachment structures comprise one or more strands of rings that are adapted to receive a fixation device.

11. The implant as recited in claim 8, wherein the one or more attachment structures comprise a portion of mesh extending from the encased mesh and the porous thermoplastic matrix of the implant.

12. The implant as recited in claim 8, wherein the one or more attachment structures comprise an angled bracket.

13. The implant as recited in claim 1, wherein the implant is provided in a particular shape to approximately fit a particular surgical site.

14. The implant as recited in claim 1, wherein the implant further comprises cells or biologically active molecules.

15. The implant as recited in claim 1, wherein the implant comprises openings, grooves, or channels that are adapted to accommodate nerves or vessels that may lie underneath the implant during use.

16. The implant recited in claim 1, wherein the implant is provided in a kit of implants having varied features.

17. The implant of claim 16, wherein the varied features comprise one or more of varied thicknesses, mesh patterns, strengths, sizes, shapes, malleability, seeding options, or combinations thereof.

18. The implant of claim 1, wherein the metal mesh is sized to allow load bearing reconstructions of the mandible or long bones, and the thermoplastic matrix provides volume filling capacity for resected or deficient bony structures, further comprising a non-porous barrier surface on at least the first or second surface of the implant.

19. The implant of claim 1, wherein the surgical grade metal mesh has shape memory.

20. The implant of claim 1, wherein the surgical grade metal mesh comprises wire screen, expanded metal, perforated metal sheet, perforated bars, an interconnected meshwork of perforated bars, a three-dimensional grid, a free form solid, a perforated or machined shaped sheet, or any combination thereof.

21. A surgical implant for bone repair comprising a matrix of porous polyethylene having an interconnected pore structure throughout the matrix and a surgical grade metal mesh embedded in the matrix such that the porous polyethylene matrix fills spaces within the mesh and encases the mesh, wherein all surfaces of the matrix comprise pores that are sized between 20-500 microns, the implant further comprising one or more attachment structures extending from the implant and adapted to attach the implant to bone, and wherein the implant is able to be bent or displaced by manipulation by hand such that the implant will generally maintain the shape to which it has been bent or displaced in a rigid and fixed position for attachment to bone, wherein the mesh provides a structure for attachment to bone.

22. The surgical implant of claim 21, wherein the implant further comprises a first surface and a second surface with a layer of a non-porous polyethylene on the porous polyethylene matrix forming the first and second surfaces.

23. The implant as recited in claim 21, wherein the one or more attachment structures comprise one or more strands of rings that are adapted to receive a fixation device, one or more angled brackets, or at least a portion of the mesh extending away from the encased mesh and the matrix of porous polyethylene.

24. A surgical implant for bone repair comprising a matrix of porous polyethylene having an interconnected pore structure throughout the matrix and a surgical grade metal mesh embedded in the matrix such that the porous polyethylene matrix fills spaces within the mesh and encases the mesh, the implant having a first surface and a second surface, wherein the first surface comprises a non-porous layer of polyethylene on the porous polyethylene matrix and the second surface and all other sides of the implant comprise the matrix of porous polyethylene with pores that are sized between 20-500 microns, the implant further comprising one or more attachment structures extending from the implant and adapted to attach the implant to bone, and wherein the implant is able to be bent or displaced by manipulation by hand such that the implant will generally maintain the shape to which it has been bent or displaced in a rigid and fixed position for attachment to bone, wherein the mesh provides a structure for attachment to bone.

25. The implant as recited in claim 24, wherein the one or more attachment structures comprise one or more strands of rings that are adapted to receive a fixation device, one or more angled brackets, or at least a portion of the mesh extending away from the encased mesh and the matrix of porous polyethylene.

* * * * *